United States Patent [19]

Morino et al.

[11] Patent Number: 5,360,822
[45] Date of Patent: Nov. 1, 1994

[54] SULFONANILIDE DERIVATIVES AND MEDICINE

[75] Inventors: Akira Morino; Iwao Morita, both of Kyoto; Shin-ichi Tada, Shiga, all of Japan

[73] Assignee: Nippon Shinyaku Co. Ltd., Japan

[21] Appl. No.: 171,195

[22] Filed: Dec. 21, 1993

Related U.S. Application Data

[63] Continuation of Ser. No. 917,097, Aug. 4, 1992, abandoned.

[30] Foreign Application Priority Data

Feb. 7, 1990 [JP] Japan ................ 2-27675
May 25, 1990 [JP] Japan ................ 2-136360
Oct. 16, 1990 [JP] Japan ................ 2-278041

[51] Int. Cl.$^5$ ............... C07C 311/08; A61K 31/18
[52] U.S. Cl. ................................. 514/605; 564/99
[58] Field of Search .................... 514/605; 564/99

[56] References Cited

FOREIGN PATENT DOCUMENTS 164865 12/1985 European Pat. Off. .
0338793 10/1989 European Pat. Off. .
0993584 5/1965 United Kingdom .
993584 5/1965 United Kingdom .
1108577 4/1968 United Kingdom .

*Primary Examiner*—Peter O'Sullivan
*Attorney, Agent, or Firm*—Rosenman & Colin

[57] ABSTRACT

An object of the present invention is to offer an agent for curing urinary incontinence with high selectivity for the urethra.

One of the compounds of the present invention is a sulfonanilide derivative having the following formula (I).

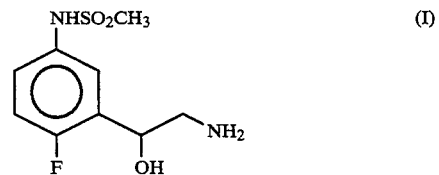

The compounds of the present invention exhibit selective contracting action to smooth muscle of the urethra tract whereupon they have useful effect as remedies for urinary incontinence.

3 Claims, No Drawings

SULFONANILIDE DERIVATIVES AND MEDICINE

This application is a continuation of co-pending application Ser. No. 917,097, filed Aug. 4, 1992, now abandoned.

TECHNICAL FIELD

The present invention relates to a compound selected from the group consisting of the compounds (I) to (VI) or optical isomer or pharmacologically-acceptable salt thereof.

A compound of the formula (I):

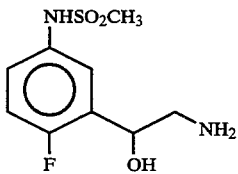

A compound of the formula (II):

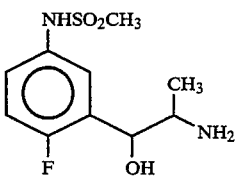

A compound of the formula (III):

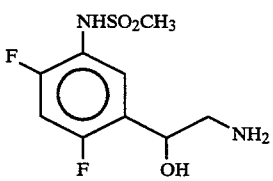

A compound of the formula (IV)

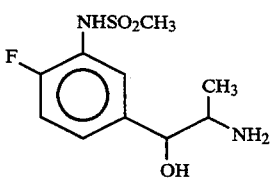

A compound of the formula (V):

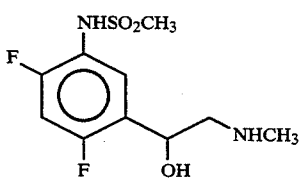

A compound of the formula (VI):

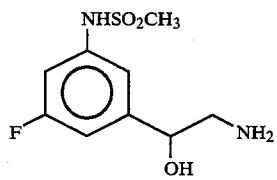

The compounds of the present invention are very useful as remedies for urinary incontinence.

BACKGROUND ART

Urinary incontinence is a symptom wherein discharge of urine via bladder and urethra cannot be done upon one's wish.

Many years have passed since therapy for aged people is to be done on an improved basis due to a significant prolongation of average human life while the frequency of occurrence of urinary incontinence of aged people who are always in bed is presumed to be about 75%. Development of remedies for urinary incontinence in order to overcome the above has been a brisk demand by the people who take care of and assist them.

At present, there has been a remarkable participation of ladies in public society. Urinary incontinence is often observed in ladies, particularly who experienced pregnancy and is a cause of anxiety for them in participating in public affairs and there is an increasing demand for remedies for urinary incontinence.

Conventional remedies for urinary incontinence such as flavoxate aim a decrease in the frequency of urinary incontinence. They act on bladder and relax it whereupon urinary incontinence is expected to alleviate.

Another type of drugs which prevent urinary incontinence based upon different action mechanism is $\alpha_1$-receptor stimulants. They accelerate the contracting action of smooth muscle of urethra for alleviating the symptom. For example, midodrine (a hypertensive agent) and norephedrine (antitussive agent) have been used mostly outside Japan.

In Examined Japanese Publications 15101/66, 06169/67 and 19500/70, there is a disclosure that the compounds having the following general formula and a part of them exhibit wide and useful pharmacological action suitable as antiinflammatory agents for preventing anaphylaxis and also as hypertensive agents for blood vessel, hypotensive agents for blood vessel, analgesics, bronchodilators, $\alpha$-receptor stimulants, $\alpha$-receptor blocking agents, $\beta$-receptor stimulants, $\beta$-receptor blocking agent and relaxants for smooth muscle (like papaverine).

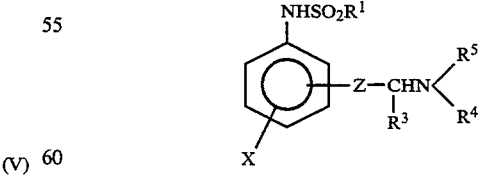

wherein X is hydrogen, hydroxy, amino, lower alkoxy, benzyloxy, halogen/methyl or $R^2SO_2NH-$; $R^1$ and $R^2$ are lower alkyl, phenyl or tolyl; $R^3$ is hydrogen or methyl; Z is C=O or CHOH; $R^4$ in $-NR^5$ ($R^4$ is hydrogen, lower alkyl or benzyl; $R^5$ is hydrogen, lower alkyl, aralkyl, ring-substituted aralkyl, aryloxyalkyl or ring-substituted aryloxyalkyl (wherein said ring-substituent is hydroxyl, methoxy or methylenedioxy; said lower alkyl and lower alkoxy have 4 or less carbon atoms; and said alkyl, ring-substituted aralkyl and ring-substituted aryloxyalkyl have 10 or less carbon atoms); and $R^4$ and $R^5$ may form pyrrolidino, morpholino or piperidino together with nitrogen atom whereby the structure stands for sulfonanilide derivative.

In addition, Examined Japanese Publication (15101/66; left column on page 12) discloses 2-fluoro-5-(2-methylamino-1-hydroxyethyl)methanesulfonanilide which is one of the compounds belonging to the above-given general formula (note: terms etc are the same as those disclosed in said patent). Said compound has the following structural formula (X):

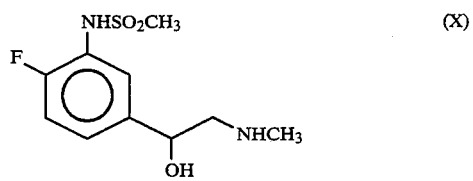

However, the pharmacological effect of the compounds disclosed in the above-given prior art literatures is a common contracting action to smooth muscle only. Accordingly, it is difficult to develop the pharmaceuticals which are helpful for the therapy of urinary incontinence.

DISCLOSURE OF THE INVENTION

It is essential for the drugs which are applicable as remedies for urinary incontinence even if they exhibit contracting action for urethral smooth muscle that (1) they exhibit selectively strong contracting action for the aimed organ (i.e. smooth muscle of urethra) as compared to the action to other organs such as peripheral blood vessel, etc. (i.e. they exhibit the so-called organ selectivity); (2) they exhibit relatively long-sustaining action even by oral administration; and (3) their toxicity to living body is low. An object of the present invention is to offer the substances having those characteristics.

The characteristic feature of the present invention is the chemical structure per se of the compounds of the present invention.

It is clear that the compound (I) of the present invention is a compound of Examined Japanese Publication 15101/66 wherein $R^1$ is methyl, X is fluorine, Z is CHOH and $R^3$, $R^4$ and $R^5$ are hydrogen. Further, the compound (I) of the present invention is a compound which is different from (X) in such an extent that (1) the fluorine is not substituted at 2 but at 4; and (2) no methyl is substituted at the amino but hydrogen remains there.

The compound (II) of the present invention is the compound of Examined Japanese Publication 15101/66 wherein $R^1$ is methyl, X is fluorine Z is CHOH, $R^3$ is methyl and $R^4$ and $R^5$ are hydrogen. Further, the compound (II) of the present invention is different from (X) in the following points that (1) fluorine is not substituted at 2 but at 4; (2) no methyl is substituted at the amino but hydrogen remains; and (3) methyl is substituted at the carbon adjacent to the amino.

The compound (III) of the present invention has two fluorine atoms substituting at the phenyl and, therefore, it is not covered by the compounds disclosed in Examined Japanese Publication 15101/66.

The compound (IV) of the present invention is the compound of Examined Japanese Publication 15101/66 wherein $R^1$ is methyl, X is fluorine, Z is CHOH, $R^3$ is methyl and $R^4$ and $R^5$ are hydrogen. Further, the compound (IV) of the present invention is different from (X) in the following respects that (1) no methyl is substituted at the amino but hydrogen remains; and (2) methyl is substituted at the carbon which is adjacent to the amino.

The compound (V) of the present invention has two fluorine atoms at the phenyl group and, therefore, it is not covered by the compounds of the Examined Japanese Publication 15101/66.

The compound (VI) of the present invention is the compound disclosed in Examined Japanese Publication 5101/66 wherein $R^1$ is methyl, X is fluorine, Z is CHOH and $R^3$, $R^4$ and $R^5$ are hydrogen. Further, the compound (VI) of the present invention is different from (X) in such respects that (1) fluorine is not substituted at 2 but at 5; and (2) no methyl is substituted but hydrogen remains there.

As fully illustrated hereinabove, the compounds of the present invention include the one which is selected from a group of the compounds disclosed in the above-given prior art patent though there is no fact that the compounds of the present invention is specifically or actually disclosed in said prior art patent. In addition, it is to be stressed that the present invention has been achieved as a result of the finding of the present inventors that those compounds exhibit specific pharmacological action. Thus, the present invention is the so-called selection invention and, therefore, it is different from the inventions disclosed in the above-given prior art patents. Moreover, the present invention is not obvious from the inventions disclosed in the above-given prior art.

It is clear from the structure formula that the compound of the present invention contains one or two asymmetric carbon(s) whereby there are 2 or 4 steric isomers. It is apparent that any and all of those optical isomer and a mixture thereof among such steric isomers are covered by the present invention.

The compounds (I) to (VI) in accordance with the present invention can be expressed by the following general formula (XI).

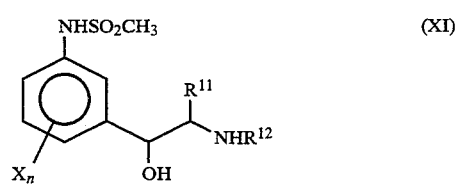

wherein $R^{11}$ and $R^{12}$ are hydrogen or methyl and $X_n$ is one or two fluorine substituent(s).

The compounds (XI) of the present invention may, for example, be manufactured by the reduction of the compound (XII) or salts thereof.

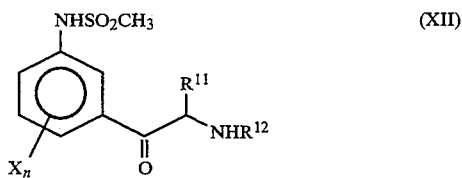

The reduction may be carried out by a known manner per se. For example, the compound (XII) or salt thereof is reduced with metal such as sodium or zinc, with metal-hydrogen complex compound such as sodium borohydride or lithium aluminium hydride; or with catalyst such as palladium or Raney nickel whereupon the racemic substance of the compound (XI) of the present invention is manufactured.

Reduction of the compound (XII) or salt thereof by metal such as sodium or zinc may, for example, be carried out by the reaction with alkali metal together with lower alcohol. Examples of the alkali metal applicable are 1 to 20 equivalents of sodium and lithium and, using 1 to 100 times as much amount of lower alcohol such as ethanol, tert-butanol or tert-amyl alcohol, the reaction is carried out at −10° C. to 120° C. for 2 to 30 hours to give the compound (XI) of the present invention.

Alternatively, amphoteric metal such as zinc and aluminium may be used together with neutral or alkaline aqueous solution. Zinc, aluminium, etc. is used in an amount of 1–20 equivalents while 5–150 times as much of 0–50% aqueous solution of sodium hydroxide, potassium hydroxide, etc. is used followed by the reaction at 5°–100° C. for 1–20 hours to manufacture the compound of the present invention.

Reduction of the compound (XII) or salt thereof with metal hydrogen complex such as sodium borohydride or lithium aluminium hydride may, for example, be carried out by dissolving in 2–100 times as much amount of protic solvent such as water, methanol, ethanol or isopropanol and reacting with 0.25–1.0 mole of sodium borohydride at −50° to 80° C. for 0.5 to 3 hours whereupon the compound (XI) of the present invention is manufactured.

In the case of lithium aluminium hydride, instead of sodium borohydride, ethers such as diethyl ether, tetrahydrofuran, 1,4-dioxane or dimethoxyethane is used instead of the above protic solvent followed by the same reaction as above.

Besides the above-given reagents, diborane, sodium cyanoborohydride, lithium aluminium triethoxyhydride and other complexes may be used as metal hydrogen complex.

In the case of catalytic hydrogenation of the compound (XII) or salt thereof, 0.5–50% (w/w) of catalyst such as palladium, Raney nickel, platinum oxide, chromium oxide, etc. is used and a suspension in 5–100 times as much aprotic solvent such-as ether, dioxane, tetrahydrofuran or ethyl acetate or protic solvent such as water, methanol, ethanol, isopropanol or acetic acid in a hydrogen atmosphere of 1–200 atm. is subjected to a catalytic hydrogenation at 0°–200° C. for 5–50 hours whereupon the compound (XI) of the present invention is manufactured.

When $R^{11}$ is hydrogen, the compound (XII) or salt thereof may be subjected to an asymmetric reduction using asymmetric ligand such as MCCPM, BINAP or BPPFOH in accordance with a method of Japanese Laid Open 01/216963 or Journal of the American Chemical Society, vol.110, page 629 (1988) or Tetrahedron Letters, page 425, 1979 to give an optical-active (XI) wherein $R^{11}$ is hydrogen. For example, 0,001–10 molar % of MCCPM-rhodium catalyst is used and a solution in 5–200 times as much of water, methanol, ethanol or other protic solvents is made to react with 0.01–10 molar % of triethylamine in a hydrogen atmosphere of 2–150 arm. for 1–100 hours to give the compound (XI) of the present invention.

The more preferred reaction condition is that the use of 0.01–0.1 molar % of MCCPM-rhodium catalyst, methanol as a solvent, 0.05–0.5 molar % of triethylamine, hydrogen pressure of 15–35 atm., the temperature of 40°–70° C. and the reaction time of 15–30 hours.

Instead of the above MCCPM-rhodium, the same reaction may be carried out using asymmetric reduction catalyst such as BINAP-ruthenium or BPPFOH-rhodium. When antipode of the asymmetric orientation is properly chosen, it is possible to manufacture optical isomers such as (R)- or (S)-substance.

The above-given optical isomer may be obtained by optical resolution of the racemic substance using optically active acid such as tartaric acid, dibenzoyltartaric acid or mandelic acid.

To be more detail, the compound of the present invention may be prepared, for example, in accordance with the following methods (1) to (10) wherein only the cases in which $R^{11}$ is hydrogen are given.

In the following formulae, Ar is as follows while X is halogen.

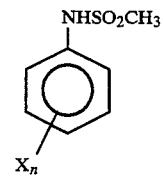

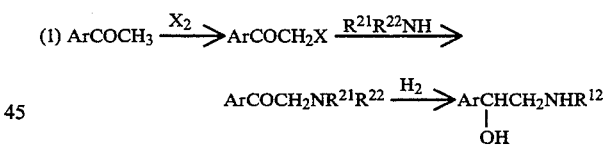

wherein $R^{21}$ is hydrogen, methyl or benzyl; $R^{22}$ is hydrogen of benzyl; and $R^{12}$ is hydrogen or methyl.

When $R^{21}$ or $R^{22}$ is benzyl in that case, debenzylation is carried out together with reduction of carbonyl whereupon the desired compound can be prepared. In some cases, reduction of carbonyl may be carried out after debenzylation or, alternatively, debenzylation may be carried out after reduction of carbonyl group.

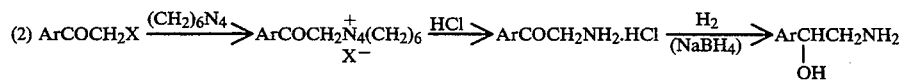

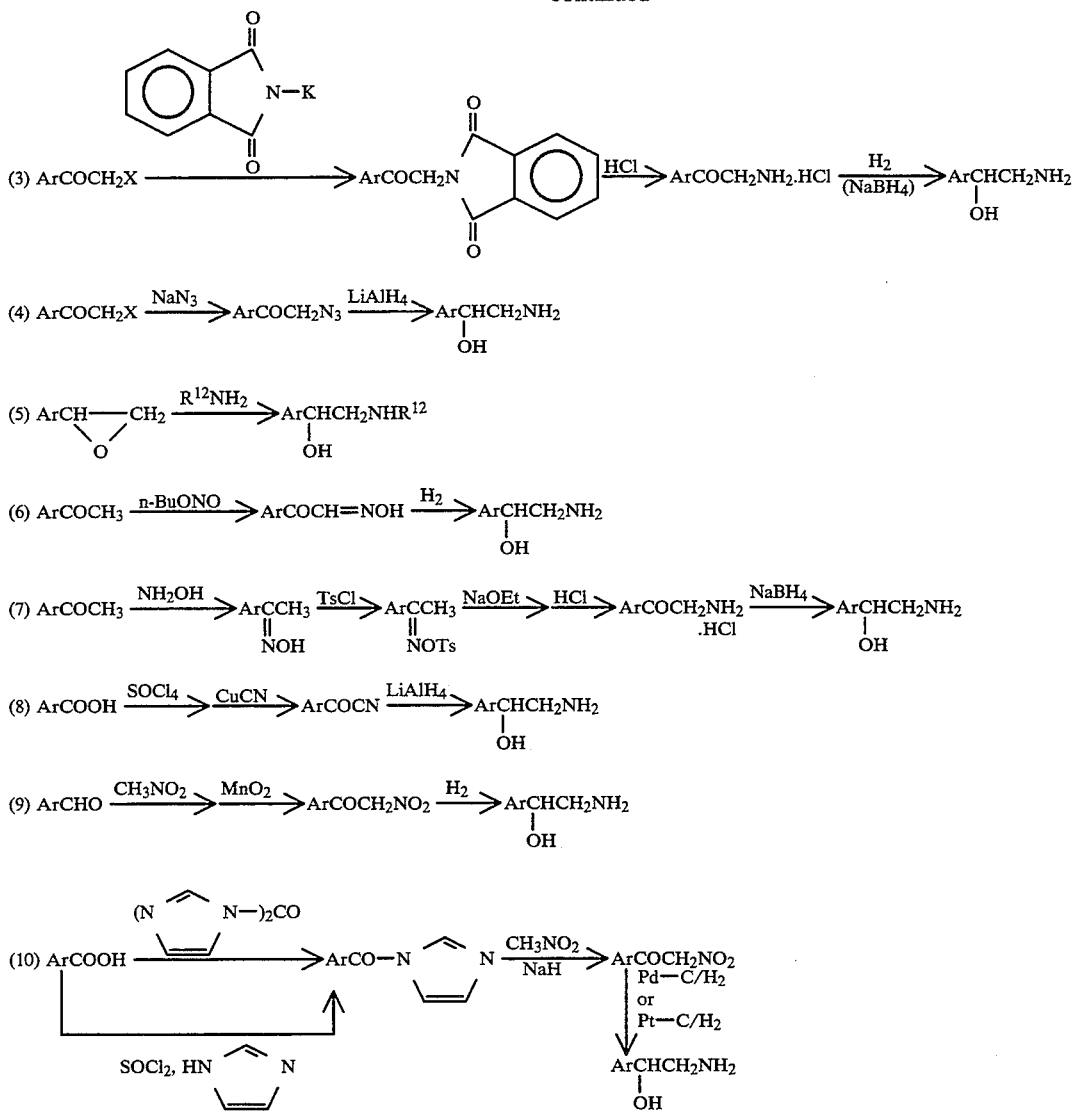
An example of the above-given manufacturing methods for the compounds of the present invention and other advantageous methods will be given as hereunder taking the case wherein fluorine is substituted at the phenyl in the compound as an example.
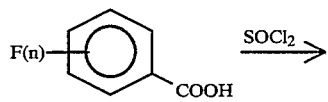
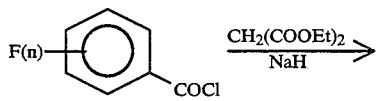
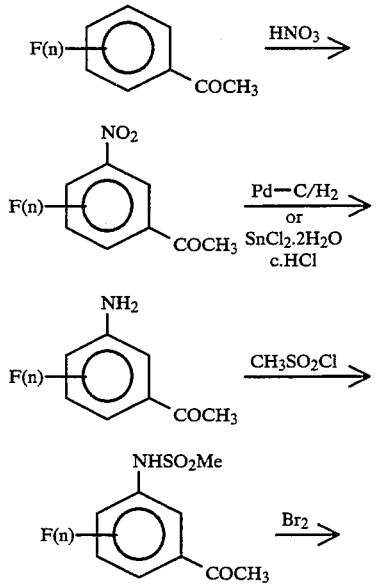

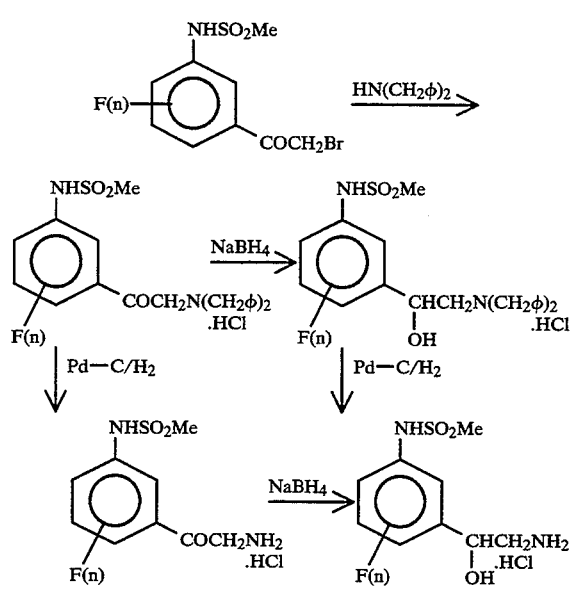

Pharmacologically-acceptable salts of the compounds of the formulae (I) to (VI) are included in the present invention. Examples of such salts are salts with mineral acid such as hydrochloric acid, hydrobromic acid, sulfuric acid and phosphoric acid and with organic acid such as acetic acid, citric acid, tartaric acid, maleic acid, succinic acid, fumaric acid, p-toluenesulfonic acid, benzenesulfonic acid and methanesulfonic acid. Hydrochloride and tartrate are particularly preferred.

When the compound of the present invention is administered as a drug, it is given to animals including human being as it is or as a pharmaceutical preparation containing, for example, 0.1–99.5% (preferably, 0.5–90%) of the compound in pharmaceutically-acceptable, nontoxic and inert carrier.

Examples of the carrier are solid, semisolid or liquid diluents, fillers and other auxiliary agents for pharmaceutical preparations and they may be used either solely or jointly. The pharmaceutical composition may be preferably administered in a form of dosage unit. The pharmaceutical composition of the present invention may be given via mouth, tissues (e.g. to vein), local parts (e.g. via skin) or rectum. Needless to say, the preparation form suitable for each administration means is to be adopted. For example, oral administration is particularly recommended.

It is recommended that the dose as a remedy for urinary incontinence is decided by taking the state of the patient (e.g. age and body weight), administering route and nature and state of the disease into consideration but, usually, the effective dose of the present invention compound is 0.01 mg to 1 g/day or, preferably, 0.1 mg to 300 mg/day for human being. In some cases, less amount will be sufficient while, in some other cases, more amount will be necessary. It is desired that the preparation is dividedly given, e.g. 2 to 3 times daily.

Oral administration may be carried out using unit dosage form in solid or liquid state such as, for example, powder, diluted powder, tablets, sugar-coated tablets, capsules, granules, suspensions, solutions, syrups, drops, sublingual tablets, and other forms.

Powder may be manufactured by making the active substance into suitable fine sizes. Diluted powder may be manufactured by making the active substance into suitable fine sizes followed by mixing with edible carbohydrate such as starch or mannitol or others. If necessary, seasoning agents, preservatives, dispersing agents, coloring agents, perfumes or others may be added thereto.

Capsules may be manufactured as follows. Thus, the powder or diluted powder prepared as above or the granules (which will be mentioned in the item of tablets) is/are filled in capsule sheaths such as gelatin capsule. It is also possible that lubricants or fluidizing agents (e.g. colloidal silica, talc, magnesium stearate, calcium stearate and solid polyethylene glycol) are mixed with the substance in the powdery state and then the mixture is filled in the capsules. When disintegrating agents or solubilizing agents such as carboxymethylcellulose, carboxymethylcellulose calcium, lowly-substituted hydroxypropylcellulose, calcium carbonate, sodium carbonate, etc. are added thereto, the effectiveness of the active substance when the capsules are taken may be improved.

It is also possible that the fine powder of the compound of the present invention is suspended/dispersed in vegetable oil, polyethylene glycol, glycerol or surface active agent and the suspension/dispersion is packed in gelatin sheet to prepare soft capsules.

Tablets may be manufactured as follows. Thus, the powder mixture is first prepared, then made into granules or slugs and disintegrating agent or lubricant is added thereto followed by tabletting.

Powder mixture which is prepared by mixing the properly-pulverized substance is mixed with the above-given diluents or base and, if necessary, together with binders (e.g. carboxymethylcellulose sodium, alginates, gelatin, polyvinylpyrrolidone and polyvinyl alcohol), solubilization-retardants (e.g. paraffin), reabsorbers (e.g. quaternary salts) and adsorbents (e.g. bentonite, kaolin and dicalcium phosphate). Powder mixture may be first wetted with a binder such as syrup, starch paste, gum arabic, cellulose solution or polymer solution and then compulsorily sieved through a sieve to give granules. In place of granulating the powder as such, the powder may be first subjected to tabletting and the resulting slug of incomplete shape is pulverized to give granules.

The granules prepared as such may be mixed with lubricants such as stearic acid, stearates, talc, mineral oil and the like so that sticking each other can be prevented. The lubricated mixture is then made into tablets.

Alternatively, the drug may be mixed with flowing inert carrier followed by making into tablets directly instead of preparation of granules and slugs as above. Transparent or semitransparent protective coating comprising closed membrane of shellac, coating by sugar of polymer materials or brushing coating comprising wax may be applied as well.

Other oral administrative preparations such as solutions, syrups and elixirs may be made into dosage unit form wherein its certain amount contains certain amount of the drug. Syrup is manufactured by dissolving the compound into a proper aqueous solution having good sweet taste while elixir is manufactured by the use of nontoxic alcoholic carrier. Suspension may be prepared by dispersing the compound into nontoxic carrier. If necessary, solubilizing agents or emulsifiers (e.g. ethoxylated isostearyl alcohols and polyoxyethylene sorbitol esters), preservatives, and seasonings (e.g.

peppermint oil and saccharine) and others may be used as well.

If necessary, the unit dosage form for oral administration may be made into microcapsules. Further, said preparations may be coated or endbedded in polymers or in wax so that prolongation of the acting time or sustained release can be expected.

Parenteral administration may be carried out by means of liquid unit dosage form (e.g. solution or suspension) for subcutaneous, intramuscular or intravenous injection. They may be manufactured by suspending or dissolving certain amount of the compound into nontoxic liquid carrier (e.g. aqueous or oily medium) suitable for the object of the injection followed by sterilizing said suspension or solution. Alternatively, certain amount of the compound is taken in a vial and then said vial and the content therein may be sterilized followed by tightly sealing. For an object of dissolution or mixing immediately before the administration, preliminary vials or carrier may be attached to the powdery or lyophilized effective substance. In order to make the injection solution isotonic, nontoxic salt or salt solution may be added thereto. If further necessary, stabilizers, preservatives, emulsifiers and the like may be used jointly.

Rectal administration may be carried out using suppositories prepared by mixing the compound with a low-melting and water-soluble or water-insoluble solid such as polyethylene glycol, cacao butter, higher esters (e.g. myristyl palmirate) and a mixture thereof.

The drug in accordance with tile present invention may be compounded with or-used together with other drugs such as other remedies for pollakisuria or for urinary incontinence.

The test examples for pharmacological effects of the compounds of the present invention will be as hereunder.

I. Action on preparation of smooth muscle of urethra and femoral artery.

The experiment was conducted using female rabbits of 2 to 3.5 kg body weight.

The animals were killed by draining the blood out under anesthetizing with pentobarbital (30 mg/kg, by intravenous injection) and smooth muscle of urethra and femoral artery were excised. Each of the excised samples was placed in a Magnus vessel filled with a modified Krebs solution (at 37° C.; under mixed gas) and both smooth muscle of urethra and femoral artery were suspended with 1 g load.

The drug to be tested was accumulated to contract the samples whereby the concentration/response curves were obtained wherefrom $ED_{50}$ (M) and $pD_2$ were calculated and the selectivity to urethra was determined. The result is given in the following table.

| Substance Tested | $pD_2$ ($ED_{50}$; $\times 10^{-6}$M) | | Selectivity (B/A) |
| --- | --- | --- | --- |
| | Urethra (A) | Femoral Artery (B) | |
| Compound of this Invention | 5.36 (4.41) | 5.49 (3.21) | 0.73 |
| Phenylephrine | 5.43 (3.75) | 6.32 (0.48) | 0.13 |
| Amidephrine | 4.97 (10.8) | 5.71 (1.96) | 0.18 |

The compound of this invention as used hereinabove was the compound (49B) or (R)-(−)-3'-(2-amino-1-hydroxyethyl)-4'-fluoromethanesulfonanilide hydrochloride (the compound of Example 5) which will be given later.

The selectivity of the compound of the present invention to urethra was about 4 to 6 times as high as those of phenylephrine and amidephrine. Consequently the compound of the-present invention exhibits quite sure selectivity to organs and its usefulness as a remedy for urinary incontinence is clear.

II. Action to $\alpha_1$-adrenoceptors

Preparation of the receptor membrane was conducted as follows. Rats were decapitated, brain except cerebellum was excised, weighed, 40 times as much 50 mM Tris-hydrochloric acid buffer (pH: 7.4) was added and the mixture was homogenized with a Polytron homogenizer and centrifuged for 20 minutes at 39,000 x g. Buffer solution was added to the precimitate and the resulting suspension was again centrifuged for 20 minutes. Then the precipitate was suspended in 40 volumes of Tris-hydrochloric acid buffer to prepare a receptor sample. The above operations were all conducted at 4° C.

$\alpha_1$-Adrenoceptor binding assay was conducted as a radioactive ligand using a [$^3$H]-prazosin.

First, the receptor sample prepared as above was incubated in 50 mM Tris-hydrochloric acid buffer (pH 7.4) with [$^3$H]-prazosin (0.2 nM) at 25° C. for 30 minutes. After incubation, the reaction solution was filtered through a glass fiber filter paper (Whatman GF/B) under vacuum. The filter paper was washed 3 times with 3 ml of ice-cold buffer, placed in a vial bottle and 10 ml of scintillator was added. The mixture was allowed to stand at room temperature for not shorter than about 10 hours and the radioactivity was measured with a liquid scintillation counter to give a total binding.

The same reaction as above was conducted in the presence of 1 $\mu$M of prazosin as well and the resulting radioactivity was defined as nonspecific binding. The difference between the total and nonspecific bindings was defined as a specific binding. All of the above experiments were carried out in duplicate.

The inhibition activity of the test drug to the [$^3$H]-prazosin binding was calculated by measuring the amount of the specific [$^3$H]-prazosin binding in the presence of various concentrations of the drug. The concentration of the drug by which the specific binding of [$^3$H]-prazosin was inhibited to an extent of 50% was defined as $IC_{50}$. The result is given below.

| Drug Tested | $IC_{50}$ |
| --- | --- |
| Compound of this Invention | $0.77 \times 10^{-5}$M |
| Phenylephrine | $4.1 \times 10^{-5}$M |
| Amidephrine | $1.8 \times 10^{-5}$M |

The compound of this invention used hereinabove was (R)-(−)-3'-(2-amino -hydroxyethyl)-4'-fluoromethanesulfonanilide hydrochloride [compound (49B); the compound of Example 5].

The inhibiting action of the compound of this invention to binding of [$^3$H]-prozosin was very strong—about twice and about five times as much stronger than amidephrine and phenylephrine. Thus, the significant affinity in binding of the compound of this invention to $\alpha_1$-adrenoceptor was quite clear.

III. Action to Intra urethral pressure and to Blood Pressure.

The experiment was conducted using male rabbits of body weight of 1.4–3.1 kg under fasted condition. The animals were fixed at backs under urethane(1.2 g/kg s.c.) anesthesia, abdomen was subjected to a midline incision and bladder was exposed. In order to prevent the urine stored in the bladder on the intra urethra pressure, the urine in the bladder was compulsorily discharged out of the body. After that, a catheter was inserted into both ureters and the urine discharged from kidney was introduced outside.

The intra urethral pressure (IUF) at the urethra tract of about 0.5–1 cm distance from the neck of the bladder was measured using a microtip transducer equipped with a balloon (filled with physiological saline solution) at the top end. Further, polyethylene tube was inserted into femoral artery to measure the blood pressure (BP).

IIIa. In the case of intravenous administration.

The drug to be tested was injected into the vein of ear every fifteen minutes and the maximum responses of the increasing action of intra urethral pressure tract and of the increasing action of blood pressure were measured at each dose. Depending upon the maximum response value at each dose, the dose increasing the urinary inner pressure to an extent of 150% [IUP(ED$_{150\%}$ ↑)] and the dose increasing the blood pressure to an extent of 30% [BP(ED$_{30\%}$ ↑)] were calculated by means of a least squares method and the result is given in the following table.

| Tested Drug (Compound No.) | IUP (A) (mg/kg, i.v.) | BP (B) | Selectivity (B/A) |
|---|---|---|---|
| (24A) | 0.035 | 0.036 | 1.0 |
| (24B) | 0.019 | 0.019 | 1.0 |
| (49A) | 0.020 | 0.044 | 2.2 |
| (49B) | 0.009 | 0.048 | 5.3 |
| (49K) | 0.009 | 0.059 | 6.6 |
| (59A) | 0.044 | 0.083 | 1.9 |
| (61A) | 0.031 | 0.037 | 1.2 |
| (63A) | 0.065 | 0.19 | 2.9 |
| (67A) | 0.070 | 2.93 | 4.2 |
| (70A) | 0.028 | 0.10 | 3.6 |
| (71A) | 0.045 | 0.095 | 2.1 |
| (73A) | 0.027 | 0.081 | 3.0 |
| Phenylephrine | 0.037 | 0.019 | 0.5 |

Each compound No. in the above list shows each of the following compound, respectively.

(24a): (±)-3'-(2-Amino-1-hydroxyethyl)methanesulfonanilide hydrochloride;

(24b): (R)-(−)-3'-(2-Amino-1-hydroxyethyl)methanesulfonanilide hydrochloride;

(49A): (±)-3'-(2-Amino-1-hydroxyethyl)-4'-fluoromethanesulfonanilide hydrochloride (the compound of Example 2);

(49B): (R)-(−)-3'-(2-Amino-1-hydroxyethyl)-4'-fluoromethanesulfonanilide hydrochloride (the compound of Example 5);

(49K): (R)-(−)-3'-(2-Amino-1-hydroxyethyl)-4'-fluoromethanesulfonanilide L-(+)-tartrate (the compound of Example 4);

(59A): (+)-erythro-3'-(2-Amino-1-hydroxypropyl)-4'-fluoromethanesulfonanilide hydrochloride (the compound of Example 6);

(61A): (±)-2'-Fluoro-5'-(1-hydroxy-2-methylaminoethyl)methanesulfonanilide hydrochloride;

(63A): (+)-5'-(2-Amino-1-hydroxyethyl)-2',4'-difluoromethanesulfonanilide hydrochloride (the compound of Example 9);

(67A): (±)-4'-Chloro-3'-(1-hydroxy-2-methylaminoethyl)methanesulfonanilide hydrochloride;

(70A): (±)-erythro-5'-(2-Amino-1-hydroxypropyl)-2'-fluoromethanesulfonanilide hydrochloride (the compound of Example 8);

(71A): (±)-2',4'-Difluoro-5'-(1-hydroxy-2-methylaminoethyl)methanesulfonanilide hydrochloride (the compound of Example 7); and (73A): (±)-3'-(2-Amino-1-hydroxyethyl)-5'-fluoromethanesulfonanilide hydrochloride (the compound of Example 11).

In the compound numbers given hereinabove, (A) is hydrochloride of racemic substance; (B) is hydrochloride of (R)-(−)-substance; and (K) is tartrate of (R)-(−)-substance and the numerals stand for the following compounds.

(24): the compound (XX)
(49): the compound (I)
(59): the compound (II)
(61): the compound (X)
(63): the compound (III)
(67): the compound (XXX)
(70): the compound (IV)
(71): the compound (V)
(73): the compound (VI)

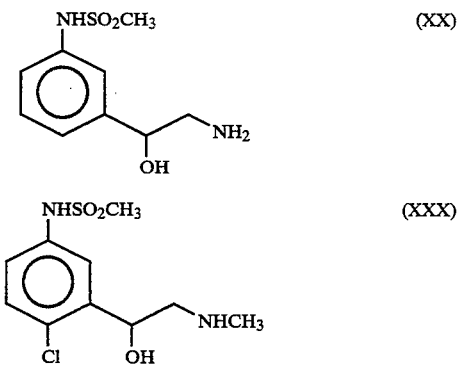

IIIb. In the case of administration to duodenum.

Abdomen right above stomach was subjected to a midline incision and, after that, the drug to be tested suspended in 0.5% methyl cellulose (0.5% MC) was administered at the dose of 0.5 ml/kg to the duodenum. After the administration, the changes in intraurethral pressure (IUP) and in blood pressure (BP) were measured with an elapse of time and the result is given in the following table. The above administration to duodenum corresponded to oral administration as the administration into digestive organ in anethetized animals.

| Tested Drug (Compd. No.) | | Dose mg/kg i.d. | No. | Change (%) Time after administration | | | | | | |
|---|---|---|---|---|---|---|---|---|---|---|
| | | | | 10 | 20 | 30 | 60 | 90 | 120 | 180 min. |
| Control | IUP | — | 1 | 2.4 | 0.4 | 0.3 | −1.6 | −0.4 | 1.0 | −4.9 |
| | BP | — | 2 | 2.1 | −0.8 | −3.6 | −7.2 | −9.9 | −12.3 | −17.2 |
| Compd. of the Invention (49B) | IUP | 0.1 | 3 | 10.5 | 11.0 | 20.7 | 29.4 | 28.9 | 30.3 | 24.1 |
| | | 0.3 | 4 | 2.15 | 44.2** | 65.2* | 84.1** | 114.9* | 101.5** | 95.7** |
| | BP | 0.1 | 5 | 2.7 | 1.9 | 3.3 | 0.5 | −5.0 | −9.8 | −14.9 |

-continued

| Tested Drug | | Dose mg/kg | | Change (%) Time after administration | | | | | | |
| (Compd. No.) | | i.d. | No. | 10 | 20 | 30 | 60 | 90 | 120 | 180 min. |
|---|---|---|---|---|---|---|---|---|---|---|
| | | 0.3 | 6 | 2.8 | 4.0 | 4.7 | 7.9** | 6.5** | 3.3* | −10.0 |
| Amidephrine | IUP | 1 | 7 | 0.7 | 0.6 | 8.3 | 47.6** | 56.8** | 46.1* | 32.1 |
| | | 3 | 8 | −4.5 | 15.9 | 47.1** | 108.5** | 107.8** | 92.7** | 92.2** |
| | BP | 1 | 9 | 2.4 | −0.1 | 2.2 | 7.2* | 14.3** | 10.3* | 3.7** |
| | | 3 | 10 | 5.8 | 3.7 | 4.1 | 20.7** | 34.4** | 39.1** | 31.1** |

*$P < 0.05$,
**$P < 0.01$
(Dunnett's method)

IV. Acute Toxicity.

Numbers of mice (ddY-strain, male, 6–8 weeks age) and rats (SD strain, male, 6–7 weeks age) in each group were 4 and 6, respectively.

The drug to be tested was orally administered at the dose of 10 ml/kg using an oral probe to the animals which were fasted since one day before (for 16–18 hours). After giving the drug, the animals were returned to the state where both feed and water were available and the general symptom and the dead cases, if any, were checked for two weeks. The drug was suspended in physiological saline solution containing 0.5% of methylcellulose (0.5% MC) and the suspension was given to the animals by oral route. The result is given in the following table.

| | Mice | | Rats | | |
|---|---|---|---|---|---|
| Compd No. | Dose (mg/kg) | Dead/ Total | Dose (mg/kg) | Dead/ Total | $LD_{50}$ (mg/kg) |
| (24A) | 1000 | 0/4 | 30 | 0/6 | |
| | 3000 | 3/4 | 100 | 1/6 | >300 |
| | | | 300 | 1/6 | |
| (24B) | 1000 | 0/4 | 5 | 0/6 | |
| | | | 10 | 2/6 | 23.2 |
| | | | 30 | 4/6 | (10.5 |
| | | | 100 | 5/6 | ~66.9) |
| (49A) | 1000 | 0/4 | 100 | 0/6 | >500 |
| | | | 500 | 1/6 | |
| (49B) | 1000 | 0/4 | 500 | 0/6 | |
| | 3000 | 0/4 | 1000 | 0/6 | >1000 |
| (49K) | 1000 | 0/4 | 100 | 0/6 | |
| | 3000 | 0/4 | 300 | 0/6 | >1000 |
| | | | 500 | 2/6 | |
| | | | 1000 | 1/6 | |
| (59A) | | | 100 | 0/6 | >100 |
| (61A) | | | 300 | 0/6 | >300 |
| (61B) | | | 3 | 0/6 | |
| | | | 10 | 2/6 | |
| | | | 30 | 1/6 | 36.1 |
| | | | 100 | 5/6 | (15.8 |
| | | | 300 | 6/6 | ~83.3) |
| (63A) | | | 300 | 0/6 | >300 |
| (67A) | | | 300 | 0/6 | >300 |
| (70A) | | | 300 | 2/6 | >300 |
| (71A) | | | 300 | 0/6 | >300 |
| (73A) | | | 100 | 1/6 | Ca. 200 |
| | | | 300 | 5/6 | |
| Amidephrine | 1000 | 0/4 | 5 | 0/6 | |
| | 3000 | 3/4 | 10 | 3/6 | 12.4 |
| | | | 20 | 4/6 | (7.8 |
| | | | 30 | 6/6 | ~18.4) |

The overall evaluation was made on the result of III. (Action to intraurethral pressure and to blood pressure) and IV (acute toxicity).

In IIIa, the selectivity of the compounds (XX) [(24A) and (24B)] was 1.0 and was with little selectivity to organs. In addition, (24B) was with significantly high acute toxicity (as high as 23.2 mg/kg) and, therefore, it was not able to be used as a pharmaceutical. Thus, that is not capable of the present invention.

The compounds (I) [(49A), (49B) and (49K)] were with selectivity of 6.6 at the highest showing sufficient organ selectivity. Moreover, the action to intraurethral pressure was 0–009 mg/kg at the highest. Thus, they exhibited satisfactory action and well low toxicity.

Selectivity of the compound (II) [(59A)] was 1.9 which is about four times as much organ selectivity when compared with known phenylephrine. In addition, the action to intraurethral pressure was as satisfactory as 0.044 mg/kg. Moreover, the acute toxcity is well low.

The compounds (X) [(61A) and (61B)] were not able to be used as pharmaceuticals and were not capable of the present invention because the selectivity of (61A) was not so high (1.2) and the acute toxicity of (61B) in terms of $LD_{50}$ was as high as 36.1 mg/kg.

Selectivity of the compound (III) [(63A)] was 2.9 which was about six times higher as compared with that of phenylephrine. Moreover, its action to intraurethral pressure was as good as 0.065 mg/kg and its toxicity was well low.

Selectivity of the compound (XXX) [(67A)] was as good as 4.2. However, its action to intraurethral pressure was as low as 0.70 mg/kg which is only about 1/20 of the known drug. Accordingly, although the toxicity was low, it was not capable of this invention.

Selectivity of the compound (IV) [(70A)] was 3.6 which was about seven times higher as compared with that of phenylephrine. Moreover, the action to intraurethral pressure was as good as 0,028 mg/kg and toxicity was well low.

Selectivity of the compound (V) [(71A)] was 2.1 which was about four times higher as compared with that of phenylephrine. Moreover, the action to intraurethral pressure was as good as 0,041 mg/kg and toxicity was well low.

Selectivity of the compound (VI) [(73A)] was 3.0 which was about six times higher as compared with that of phenylephrine. Moreover, the action to intraurethral pressure was as good as 0.027 mg/kg and toxcity was well low.

In the experiments by administration to digestive organ for checking the effect by oral administration, the dose of the representative compound of the present invention (49B) resulting in intraurethral pressure increasing action of the same grade as known amidephrine was about one-tenth. Moreover, the increase in blood pressure was little and such an action was sustained for long time.

Out of the above-given result, the following eight substances were able to be chosen as the compounds of the present invention. Thus, (49A), (49B), (49K), (59A), (63A), (70A), (71A) and (73A).

EXAMPLES

The present invention will be further illustrated by way of the referential examples and working examples concerning the manufacture of the compounds of the present invention and also manufacturing examples of the drugs of the present invention.

REFERENTIAL EXAMPLE 1

(1) 5'-Amino-2'-fluoroacetophenone (28 g) was dissolved in a mixture of 100 ml of ethyl acetate and 15.9 g of pyridine, a solution of 23 g of methanesulfonyl chloride in 50 ml of ethyl acetate was added with ice-cooling and stirring and the mixture was made to react at room temperature for 3 hours. The reaction mixture was washed with water, dried, the solvent was evaporated therefrom and the residue was purified by silica gel column chromatography (eluting with chloroform) to give 33.7 g of 3'-acetyl-4'-fluoromethanesulfonanilide, m.p. 120°–123° C.

(2) 3'-Acetyl-4'-fluoromethanesulfonanilide (32 g) was dissolved in 250 ml of acetic acid, then 22.1 g of bromine was dropped thereinto gradually at room temperature and the mixture was made to react at room temperature for 3 hours. The reaction mixture was added to ice water and the mixture was extracted with ethyl acetate. The extract was washed with aqueous solution of sodium bicarbonate, then with water, dried and the solvent was evaporated therefrom followed by crystallizing from diisopropyl ether to give 38 g of 3'-(2-bromoacetyl)-4'-fluoromethanesulfonanilide, m.p. 110°–113° C.

(3) 3'-(2-Bromoacetyl)-4'-fluoromethanesulfonanilide (30 g) was dissolved in 200 ml of N,N-dimethylformamide, a solution of 38 g of dibenzylamine in N,N-dimethylformamide was added with ice-cooling and stirring and the mixture was made to react at room temperature for 1 hour. The reaction mixture was added to water followed by extracting with ethyl acetate. The extract was washed with water, dried, the solvent was evaporated therefrom and the residue was crystallized from diisopropyl ether to give 35 g of 3'-(2-dibenzylaminoacetyl)-4'-fluoromethanesulfonanilide. The crystals were made into hydrochloride to give 35 g of crystals, m.p. 185°–188° C.

(4) 3'-(2-Dibenzylaminoacetyl)-4'-fluoromethanesulfonanilide hydrochloride (10 g) was suspended in 100 ml of methanol, 1.0 g of 5% palladium carbon was added thereto and the mixture was reduced at room temperature at the hydrogen pressure of 8 atm. The catalyst was removed, the solvent was removed and the crystals separated out therefrom were collected by filtration to give 4.6 g of 3'-(2-aminoacetyl)-4'-fluoromethanesulfonanilide hydrochloride, m.p. 177°–181° C.

NMR spectra (DMSO-$d_6$) δ: 2.96 (3 H, s), 4.23–4.5 (2 H, m), 7.0–8.0 (3 H, m), 8.2–8.9 (3 H, broad), 9.55–10.2 (1 H, broad)

The following compounds were obtained by the same manner as in (1) to (3) of Referential Example 1.

REFERENTIAL EXAMPLE 2

3'-(2-Dibenzylaminopropionyl)-4'-fluoromethanesulfonanilide

NMR spectra (CDCl$_3$) δ: 1.34 (3 H, d, J=6.4 Hz), 3.01 (3 H, s), 3.59 (4 H, s), 4.23 (3 H, q, J=6.4 Hz), 6.91–7.52 (13 H, m).

REFERENTIAL EXAMPLE 3

5'-(2-Dibenzylaminopropionyl)-2'-fluoromethanesulfonanilide.

NMR Spectra (CDCl$_3$) δ: 1.32 (3 H, d, J=7.0 Hz), 2.99 (3 H, s), 3.59 (4 H, d, J=3.5 Hz), 4.22–4.33 (2 H, m), 7.23 (13 H, m).

REFERENTIAL EXAMPLE 4

5'-(2-Dibenzylaminoacetyl)-2',4'-difluoromethanesulfonanilide M.p. 168°–172° C.

REFERENTIAL EXAMPLE 5

5'-(2-Benzylmethylaminoacetyl)-2',4'-difluoromethanesulfonanilide.

NMR spectra (CDCl$_3$, DMSO-$d_6$) δ: 2.34 (3 H, s), 2.95 (3 H, s), 3.64–3.98 (4 H, m), 7.19–7.31 (7 H, m).

REFERENTIAL EXAMPLE 6

(1) 2-Fluoro-5-nitrobenzoic acid (60 g) was suspended in 300 ml of methanol, 6.0 g of 5% palladium-carbon was added thereto and the mixture was reduced at 40° C. with hydrogen pressure of 6.5 atm. The catalyst was removed, the solvent was evaporated and the crystals separated out therefrom were filtered to give 42 g of 5-amino-2-fluorobenzoic acid, m.p. 189°–192° C.

NMR spectra (DMSO-$d_6$) δ: 6.65–7.25 (3 H, m), 5.5–7.5 (3 H, broad).

(2) 5-Amino-2-fluorobenzoic acid (100 g) was suspended in 1.3 liters of methanol, 100 g of concentrated hydrochloric acid was gradually added thereto and the mixture was heated to reflux for 24 hours. Methanol was evaporated and the residue was poured into ice water, the mixture was neutralized with sodium bicarbonate and extracted with ethyl acetate. The extract was washed with water, dried and evaporated. The crystals separated out therefrom were filtered to give 88 g of methyl 5-amino-2-fluorobenzoate.

NMR spectra (CDCl$_3$). δ: 2.9–3.8 (2 H, broad), 3.92 (3 H, s), 6.8–7.3 (3 H, m).

(3) Methyl 5-amino-2-fluorobenzoate (50 g) and 23.4 g of pyridine were dissolved in 300 ml of ethyl acetate, then 37 g of methanesulfonyl chloride was added thereto with ice-cooling and stirring and the mixture was made to react at room temperature for 3 hours. The reaction mixture was washed with water, dried, evaporated and the crystals separated out therefrom were filtered to give 72 g of methyl 2-fluoro-5-methanesulfonylaminobenzoate, m.p. 135°–137° C.

NMR spectra (CDCl$_3$) δ: 3.02 (3 H, s), 3.96 (3 H, s), 6.9–7.9 (3 H, m).

(4) Methyl 2-fluoro-5-methanesulfonylaminobenzoate (72 g) and 49 g of potassium hydroxide were dissolved in 400 ml of a 1:1 mixture of water and methanol and the solution was heated to reflux for 2 hours. Methanol was evaporated and the residue was acidified with hydrochloric acid. The crystals separated out therefrom were filtered followed by washing with water and drying to give 63 g of 2-fluoro-5-methanesulfonylaminobenzoic acid, m.p. 203°–205° C.

NMR spectra (DMSO-$d_6$) δ: 2.98 (3 H, s), 7.2–7.8 (3 H, m), 9.82 (1 H, broad s).

(5) 60% Sodium hydride (3.0 g) was suspended in 20 ml of N,N-dimethylformamide, then 8.4 g of nitromethane was gradually dropped thereinto with ice-cooling and stirring and the mixture was stirred at room temperature for 30 minutes. 2-Fluoro-5-methanesulfonylaminobenzoic acid (8.0 g) and 6.7 g of N,N'-carbonyldiimidazole were dissolved in 30 ml of N,N-dimethylformamide and the solution was made to react at room temperature for 1 hour. The reaction mixture was added, with ice-cooling, to the solution obtained hereinbefore and the mixture was stirred at room temperature for 2 hours. Then, the mixture was poured into ice water, acidified with hydrochloric acid and the crystals separated out therefrom were filtered, washed with small amount of ethanol and dried to give 8.2 g of 4'-fluoro-3'-(2-nitroacetyl)-methanesulfonanilide, m.p. 174°–176 ° C.

NMR spectra (DMSO-$d_6$). δ: 2.97 (3 H, s), 5.87 (2 H, d, J=3.5 Hz), 7.0–8.0 (3 H, m), 9.81 (1 H, broad s).

(6) 4'-Fluoro-3'-(2-nitroacetyl)methanesulfonanilide (0.5 g) was dissolved in 10 ml of methanol, then 2 ml of 10% hydrochloric acid/methanol and 50 mg of 5% palladium/carbon were added thereto and the mixture was stirred at room temperature for 21 hours in a hydrogen atmosphere of 1 atm. The catalyst was removed, the solvent was evaporated and the crystals which were separated out by addition of small amount of ethanol were filtered to give 0.4 g of 3'-(2-aminoacetyl)-4'-fluoromethanesulfonanilide hydrochloride, m.p. 179°–181° C.

NMR spectra (DMSO-$d_6$). δ: 2.96 (3 H, s), 4.23–4.5 (2 H, m), 7.0–8.0 (3 H, m), 8.2–8.9 (3 H, broad), 9.55–10.2 (1 H, broad).

The following compounds were prepared by the same manner as in (1)–(6) of Referential Example 6.

REFERENTIAL EXAMPLE 7

3'-(2-Aminoacetyl)-5'-fluoromethanesulfonanilide hydrochloride. M.p. 190°–200° C. (decompn). Elementary Analysis for $C_9H_{11}FN_2O_3S.HCl$. Calcd: C 38.24, H 4.28, N 9.91; Found: C 38.04, H 4.15, N 9.66.

NMR spectra (DMSO-$d_6$). δ: 3.09 (3 H, s), 4.53 (2 H, s), 7.37 (1 H, dt, J=11 Hz, 1.5 Hz), 7.54–7.68 (2 H, m), 8.3–10.6 (4 H, broad).

EXAMPLE 1

3'-(2-Aminoacetyl)-4'-fluoromethanesulfonanilide hydrochloride (3 g) was dissolved in 30 ml of methanol, 0.20 g of sodium borohydride was added at 0°–5° C. and the mixture was made to react at the same temperature for 1 hour. The solvent was evaporated and the residue was made into free base using ion exchange resin (Dowex 50W X2), concentrated to dryness and the residue was recrystallized from methanol to give 2.4 g of (±)-3'-(2-amino-1-hydroxyethyl)-4'-fluoromethanesulfonanilide, m.p. 176°–179° C.

EXAMPLE 2

(±)-3'-(2-Amino-1-hydroxyethyl)-4'-fluoromethanesulfonanilide (2.3 g) was treated with 20% ethanolic hydrochloric acid to give 2.4 g of (±)-3'-(2-amino-1-hydroxyethyl)-4'-fluoromethanesulfonanilide hydrochloride, m.p. 178°–181° C. Elementary analysis for $C_9H_{13}FN_2O_3S.HCl$. Calcd: C 37.96, H 4.96, N 9.84; Found: C 37.97, H 5.06, N 9.59.

EXAMPLE 3

3'-(2-Aminoacetyl)-4'-fluoromethanesulfonanilide hydrochloride (21 g) was suspended in 210 ml of methanol, then a catalyst prepared from 50 mg of (2R,4R)-N-methylcarbamoyl-4-dicyclohexylphosphino-2-diphenylphosphinomethylpyrrolidine and 18 mg of di-μ-chlorobis(cyclooctadiene)dirhodium (I) was added thereto together with 19 mg of triethylamine and the mixture was reduced at 50° C. in an atmosphere of hydrogen of 20 atm. The reaction mixture was concentrated and made into a free base using ion exchange resin (Dowex 50W X2) to give 15.8 g of crude (R)-(−)-3'-(2-amino-1-hydroxyethyl)-4'-fluoromethanesulfonanilide.

NMR spectra (DMSO-$d_6$). δ: 2.4–2.76 (2 H, m), 2.92 (3 H, s), 3.9–4.6 (2 H, broad), 4.65–4.74 (1 H, m), 5.2–5.6 (1 H, broad), 7.03–7.12 (2 H, m), 7.28–7.37 (1 H, m).

EXAMPLE 4

Crude (R)-(−)-3'-(2-amino-1-hydroxyethyl)-4'-fluoromethanesulfonanilide (15.8 g) and 9.6 g of L-(+)-tartaric acid were dissolved in water, ethanol was added thereto and the crystals separated out thereby were collected and repeatedly recrystallized from water-ethanol to give 16 g of (R)-(−)-3'-(2-amino-1-hydroxyethyl)-4'-fluoromethanesulfonanilide L-(+)-tartrate. M.p. 91°–92 ° C.

Elementary analysis for $C_9H_{13}FN_2O_3S.C_4H_6O_6.H_2O$ Calcd: C 37.49, H 5.08, N 6–73; Found: C 37.67, H 5.22, N 6.65.

$[\alpha]_D = -5.03°$ (water, c=1.033).

EXAMPLE 5

(R)-(−)-3'-(2-Amino-1-hydroxyethyl)-4'-fluoromethanesulfonanilide L-(+)-tartrate (2.0 g) was made into a free base using ion exchange resin (Dowex 50W X2) followed by treating with 20% ethanolic hydrochloric acid. The crystals which were separated out were collected to give 1.1 g of (R)-(−)-3'-(2-amino-1-hydroxyethyl)-4'-fluoromethanesulfonanilide hydrochloride, m.p. 189°–191° C.

Elementary analysis for $C_9H_{13}FN_2O_3S.HCl$. Calcd: C 37.96, H 4.96, N 9.84; Found: C 37.85, H 4.96, N 9.80.

$[\alpha]_D = -22.33°$ (water, c=1.012).

NMR spectra (DMSO-$d_6$). δ: 2.73–3.07 (2 H, m), 2.97 (3 H, s), 5.0–5.13 (1 H, m), 6.21–6.30 (1 H, broad), 7.12–7.23 (2 H, m), 7.35–7.45 (1 H, m), 7.9–8.9 (4 H, broad).

EXAMPLE 6

3'-(2-Dibenzylaminopropionyl)-4'-fluoromethanesulfonanilide hydrochloride (0.8 g) was suspended in 8 ml of methanol, then 0.08 g of 5% palladium-carbon was added thereto and the mixture was reduced at room temperature for 15 hours with hydrogen of 8 atm. The catalyst was removed followed by evaporating off the solvent to give 0.5 g of crystals. The resulting crystals were dissolved in 40 ml of methanol, 0.32 g of sodium borohydride was added to the solution with ice-cooling and stirring and the mixture was made to react for 15 minutes. The solvent was evaporating off from the reaction mixture, the residue was made into a free base using ion exchange resin (Dowex 50W X2) and the free base was recrystallized from methanol and treated with 20% ethanolic hydrochloric acid to isolate 0.27 g of (±)-erythro-3'-(2-amino-1-hydroxypropyl)-4'-fluoromethanesulfonanilide hydrochloride, m.p. 239°–241° C.

Elementary analysis for $C_{10}H_{15}FNO_3S.HCl$. Calcd: C 40.20, H 5.40, N 9.38; Found: C 39.81, H 5.35, N 9.47.

NMR spectra (DMSO-$d_6$) δ: 0.95 (3 H, d, J=7.0 Hz), 2.94 (3 H, s), 2.25–2.39 (1 H, m), 5.12–5.20 (1 H, broad), 6.24 (1 H, d, J=4.0 Hz), 7.13–7.18 (2 H, m), 7.38–7.42 (1 H, m), 8.02–8.54 (3 H, broad), 9.61–9.90 (1 H, broad).

EXAMPLE 7

5′-(2-Benzylmethylaminoacetyl)-2′,4′-difluoromethanesulfonanilide (2.5 g) was dissolved in 10 ml of tetrahydrofuran, then a solution of 0.28 g of sodium borohydride in 2 ml of water was added thereto with ice-cooling and stirring and the mixture was made to react for 15 minutes. The solvent of the reaction mixture was evaporated and the residue was extracted with ethyl acetate. The extract was washed with water, dried and evaporated and 2.7 g of the resulting (±)-5′-(2-benzylmethylamino-1-hydroxyethyl)-2′,4′-difluoromethanesulfonanilide was suspended in 90 ml of methanol. 5% Palladium-carbon (0.5 g) was added to the suspension and the mixture was reduced at 30° C. for 15 minutes with hydrogen of 8 atm. The catalyst was removed and the residue was treated with 20% ethanolic hydrochloric acid to give 1.25 g of (±)-2′,4′-difluoro-5′-(1-hydroxy-2-methylaminoethyl)-methanesulfonanilide hydrochloride, m.p. 192°–194° C.

Elementary analysis for $C_{10}H_{14}F_2N_2O_3S.HCl$. Calcd: C 37.92, H 4.77, N 8.84; Found: C 37.98, H 4.80, N 8.79.

NMR spectra ($CDCl_3$, $DMSO-d_6$). δ: 2.46 (3 H, s), 2.55–2.80 (2 H, m), 3.00 (3 H, s), 4.80–5.19 (1 H, m), 6.67–7.01 (1 H, m), 7.67–7.80 (1 H, m).

EXAMPLE 8

5′-(2-Dibenzylaminopropionyl)-2′-fluoromethanesulfonanilide hydrochloride (2.6 g) was dissolved in 50 ml of methanol, then 0.26 g of 5% palladium-carbon was added thereto and the mixture was reduced at 30° C. for 15 hours with hydrogen of 7 atm. The catalyst was removed therefrom and to the solution was added, with ice-cooling and stirring, 0.41 g of sodium borohydride followed by being made to react at room temperature for 2 hours. The solvent was evaporated therefrom and the residue was purified by means of silica gel column chromatography (eluted with chloroform and methanol). The resulting oil was treated with 20% ethanolic hydrochloric acid to give 0.7 g of (±)-erythro-5′-(2-amino-1-hydroxypropyl)-2′-fluoromethanesulfonanilide hydrochloride, m.p. 235° C.

Elementary analysis for $C_{10}H_{15}FN_2O_3S.HCl$. Calcd: C 40.20, H 5.40, N 9.38; Found: C 40.03, H 5.67, N 9.30.

NMR spectra ($CDCl_3$, $DMSO-d_6$). δ: 0.93 (3 H, d, J=7.0 Hz), 2.96 (3 H, s), 2.55–3.28 (1 H, m), 4.00–4.39 (4 H, m), 4.39–4.50 (1 H, m), 7.04–7.48 (3 H, m).

EXAMPLE 9

5′-(2-Dibenzylaminoacetyl)-2′,4′-difluoromethanesulfonanilide (1.8 g) was dissolved in 35 ml of methanol, then 0.16 g of sodium borohydride was added thereto with stirring at room temperature and the mixture was made to react at the same temperature for 1 hour. The solvent was evaporated therefrom and the residue was extracted with ethyl acetate. The extract was washed with water, dried and evaporated and the resulting residue was purified by means of silica gel column chromatography (eluted with n-hexane/ethyl acetate) to give 1.6 g of oil. The oil was dissolved in 30 ml of methanol, 160 mg of 5% palladium-carbon was added thereto and the mixture was reduced at 30 ° C. for 15 hours with hydrogen of 7 atm. The catalyst was removed, the solvent was removed from the filtrate and the residue was treated with 20% ethanolic hydrochloric acid to give 0.53 g of (±)-5′-(2-amino-1-hydroxyethyl)-2′,4′-difluoromethanesulfonanilide hydrochloride, m.p. 209°–211° C.

Elementary analysis for $C_9H_{12}F_2N_2O_3S.HCl$. Calcd: C 35.71, H 4.33, N 9.25; Found: C 35.73, H 4.59, N 9.01.

NMR spectra ($CDCl_3$, $DMSO-d_6$). δ: 2.57–2.88 (2 H, m), 2.97 (3 H, s), 4.20 (3 H, s), 4.74–4.83 (1 H, m), 6.71–7.04 (1 H, m), 7.47–7.75 (2 H, m).

EXAMPLE 10

3′-(2-Aminoacetyl)-5′-fluoromethanesulfonanilide hydrochloride (1.7 g) was suspended in 70 ml of methanol, then 114 mg of sodium borohydride was added thereto with stirring at 5°–10° C. and the mixture was stirred at room temperature for 30 minutes. The solvent was evaporated and the residue was made into a free base using ion exchange resin (Dowex 50W X2) followed by recrystallizing from methanol-ethanol to give 1.07 g of (±)-3′-(2-amino-1-hydroxyethyl)-5′-fluoromethanesulfonanilide, m.p. 167°–169° C.

Elementary analysis for $C_9H_{13}FN_2O_3S$. Calcd: C 43.54, H 5.28, N 11.28; Found: C 43.55, H 5.33, N 11.39.

EXAMPLE 11

The compound (0.70 g) obtained in Example 10 was treated with 20% ethanolic hydrochloric acid to give 0.72 g of (±)-3′-(2-amino-1-hydroxyethyl)-5′-fluoromethanesulfonanilide hydrochloride. M.p. 183°–186° C.

Elementary analysis for $C_9H_{13}FN_2O_3S.HCl$. Calcd: C 37.96, H 4.96, N 9.84; Found: C 37.72, H 5.18, N 9.97.

NMR spectra ($DMSO-d_6$). δ: 2.74–3.1 (2 H, m), 3.04 (3 H, s), 4.75–4.88 (1 H, m), 6.12–6.28 (1 H, broad), 6.86–7.12 (3 H, m), 8.24–8.86 (4 H, broad).

EXAMPLE OF THE PREPARATION 1

The compound of the present invention [the compound number (49B)] was made into pharmaceutical preparation by means of conventional method for preparing tablets using the following ingredients.

One tablet contains:

| | |
|---|---|
| The compound of the invention | 1 mg |
| Lactose | 60 mg |
| Corn starch | 30 mg |
| Crystalline cellulose | 20 mg |
| Hydroxypropylcellulose | 7 mg |
| Magnesium stearate | 2 mg |
| Total | 120 mg |

EXAMPLE FOR THE PREPARATION 2

The compound of the present invention [the compound number (49B)] was made into diluted powder by means of the conventional method for preparing the same using the following ingredients.

| | |
|---|---|
| The compound of the invention | 2 mg |
| Lactose | 988 mg |
| Aqueous silicon dioxide | 10 mg |
| Total | 1,000 mg |

EXAMPLE FOR THE PREPARATION 3

The compound of the present invention [the compound number (49B)] was made into injection solution by means of the conventional method for preparing the same using the following ingredients.

| | |
|---|---|
| The compound of the invention | 1 mg |

We claim:

1. A compound

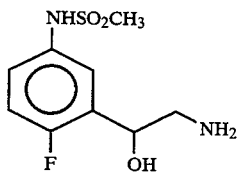
(I)

or a pharmaceutically acceptable salt or isomer thereof.

2. A method for treating urinary incontinence in animals and humans which comprises administering to an animal or human in need thereof a pharmaceutically effective amount of a compound

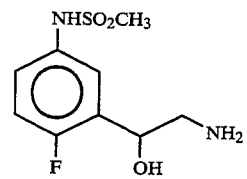
(I)

or a pharmaceutically acceptable salt or isomer thereof.

3. A pharmaceutical composition for treating urinary incontinence in animals and humans which comprises a pharmaceutically effective amount of a compound

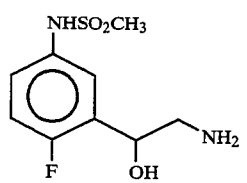
(I)

or a pharmaceutically acceptable salt or isomer thereof in combination with a pharmaceutically acceptable carrier.

* * * * *

UNITED STATES PATENT AND TRADEMARK OFFICE
CERTIFICATE OF CORRECTION

PATENT NO. : 5,360,822
DATED : November 1, 1994
INVENTOR(S) : Morino Akira et al It is certified that error appears in the above-identified patent and that said Letters Patent is hereby corrected as shown below:

Column 14, in the table below line 60, under the fifth column labelled "10", change the fourth entry from "2.15" to --21.5--.

Column 16, line 19, change "0-009" to --0.009--.

Column 20, line 22, change "6-73" to --6.73--.

Signed and Sealed this

Twentieth Day of June, 1995

BRUCE LEHMAN

Attest:

Attesting Officer

Commissioner of Patents and Trademarks